United States Patent
Hacker et al.

(10) Patent No.: US 11,890,402 B2
(45) Date of Patent: Feb. 6, 2024

(54) EXTRACORPOREAL BLOOD TREATMENT DEVICE AND METHOD FOR MONITORING THE INTEGRITY OF A DIALYZER OF AN EXTRACORPOREAL BLOOD TREATMENT DEVICE

(71) Applicant: FRESENIUS MEDICAL CARE DEUTSCHLAND GMBH, Bad Homburg (DE)

(72) Inventors: Jurgen Hacker, Neu-Anspach (DE); Soren Gronau, Russelsheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 795 days.

(21) Appl. No.: 16/476,555

(22) PCT Filed: Jan. 10, 2018

(86) PCT No.: PCT/EP2018/050597
§ 371 (c)(1),
(2) Date: Jul. 9, 2019

(87) PCT Pub. No.: WO2018/130592
PCT Pub. Date: Jul. 19, 2018

(65) Prior Publication Data
US 2019/0321533 A1    Oct. 24, 2019

(30) Foreign Application Priority Data
Jan. 13, 2017    (DE) .................... 10 2017 000 227.4

(51) Int. Cl.
  *A61M 1/16*    (2006.01)
  *B01D 65/10*    (2006.01)
  *G01M 3/32*    (2006.01)

(52) U.S. Cl.
  CPC ........ *A61M 1/1692* (2013.01); *A61M 1/1601* (2014.02); *B01D 65/102* (2013.01);
  (Continued)

(58) Field of Classification Search
  None
  See application file for complete search history.

(56) References Cited

U.S. PATENT DOCUMENTS

| | | | | |
|---|---|---|---|---|
| 5,591,344 A | * | 1/1997 | Kenley | A61M 1/3647 210/764 |
| 5,711,883 A | * | 1/1998 | Folden | B01D 65/102 73/40 |
| 2003/0136181 A1 | * | 7/2003 | Balschat | A61M 1/1601 73/40.5 R |

FOREIGN PATENT DOCUMENTS

| | | |
|---|---|---|
| EP | 1327457 A1 | 7/2003 |
| WO | 9711770 A1 | 4/1997 |

OTHER PUBLICATIONS

International Search Report and Written Opinion issued in corresponding International Patent Application No. PCT/EP2018/050597 (with English translation of International Search Report) dated Mar. 27, 2018 (11 pages).

(Continued)

*Primary Examiner* — Jonathan M Peo
(74) *Attorney, Agent, or Firm* — Kilyk & Bowersox, P.L.L.C.

(57) ABSTRACT

The invention relates to an extracorporeal blood treatment device for carrying out an extracorporeal blood treatment, in which blood flows in an extracorporeal blood circuit A through the blood chamber 2 of a dialyser 1 which is divided by a semi-permeable membrane 4 into the blood chamber 2 and a dialysate chamber 3. The invention further relates a method for monitoring the integrity of a dialyser 1. The (Continued)

blood treatment device provides a preparation mode in preparation for the blood treatment, in which the dialysate chamber 3 of the dialyser 1 (filter) is filled with a liquid, while the blood chamber 2 is not filled with blood, and a treatment mode following the preparation mode, in which blood is conveyed through the blood chamber 2. For monitoring the integrity of the dialyser 1, in the preparation mode the fluid system B including the dialysate chamber 3, or a portion of the fluid system including the dialysate chamber, is filled with a liquid. At this time, however, the blood chamber 2 is not filled with blood. After the membrane of the dialyser 1 has been wetted with liquid, liquid is removed from the fluid system B including the dialysate chamber 3 such that a low pressure p is established in the fluid system. The control and arithmetic unit 29 of the blood treatment device is so configured that the increase in the amount of the low pressure p, measured by means of a pressure measuring apparatus 34, in a given time interval is determined, and the leakage rate LR of the fluid system is determined from the increase in the amount of the low pressure in a given time interval and the compliance C of the fluid system B including the dialysate chamber 3. A lack of integrity of the dialyser is then concluded on the basis of the determined leakage rate LR.

12 Claims, 2 Drawing Sheets

(52) U.S. Cl.
CPC .. *G01M 3/3236* (2013.01); *A61M 2205/3331* (2013.01); *A61M 2205/705* (2013.01); *B01D 2311/14* (2013.01)

(56) References Cited

OTHER PUBLICATIONS

International Preliminary Report on Patentability issued in corresponding International Patent Application No. PCT/EP2018/050597 dated Jul. 16, 2019 (7 pages).

\* cited by examiner

EXTRACORPOREAL BLOOD TREATMENT DEVICE AND METHOD FOR MONITORING THE INTEGRITY OF A DIALYZER OF AN EXTRACORPOREAL BLOOD TREATMENT DEVICE

This application is a National Stage Application of PCT/EP2018/050597, filed Jan. 10, 2018, which claims priority to German Patent Application No. 10 2017 000 227.4, filed Jan. 13, 2017.

The invention relates to an extracorporeal blood treatment device for carrying out an extracorporeal blood treatment, in which blood flows in an extracorporeal blood circuit through the blood chamber of a dialyser which is divided by a semi-permeable membrane into the blood chamber and a dialysate chamber. The invention further relates to a method for monitoring the integrity of a dialyser of an extracorporeal blood treatment device.

In dialysis, the blood to be treated flows in an extracorporeal blood circuit through the blood chamber of a dialyser which is divided by a semi-permeable membrane into the blood chamber and a dialysate chamber, while dialysate flows in a fluid system through the dialysate chamber of the dialyser. The extracorporeal blood circuit has a blood supply line, which leads to the blood chamber, and a blood discharge line, which leads away from the blood chamber, and the fluid system has a dialysate supply line leading to the dialysate chamber and a dialysate discharge line leading away from the dialysate chamber. The lines can be part of a hose system which is intended for single use.

In the fluid system, at least one pump is provided for conveying the dialysate. The fresh dialysate is made available in a dialysate source, and used dialysate is discharged into a drain. In addition, blood treatment devices generally have a balancing unit for balancing fresh and used dialysate, and an ultrafiltration apparatus having an ultrafiltrate pump for removing ultrafiltrate from the fluid system. The system for supplying and discharging the dialysate, which can comprise, for example, one or more hose lines, pumps or valves, is also referred to as the hydraulic system.

During dialysis treatment, the pressure difference between the blood and the dialysate is generally positive over the length of the membrane. If the membrane of the dialyser is damaged or has defects, there is the risk that blood will pass from the extracorporeal blood circuit into the hydraulic system of the blood treatment device during the blood treatment. In this case, the known blood leak detectors provided in the hydraulic system downstream of the dialyser respond. If blood is detected in the hydraulic system, the blood treatment must be interrupted and the dialyser replaced. Complex measures for disinfecting the hydraulic system are additionally required.

For testing the tightness of a fluid system, there are known pressure hold tests in which a high pressure or a low pressure is established in the fluid system. If in a subsequent pressure hold test phase the pressure does not fall below a specific limit value or rise above a specific limit value within a given time interval, it can be concluded that the fluid system is tight.

There is known from EP 1 327 457 A1 a blood treatment device which has a monitoring apparatus for detecting a leak in the fluid system. The monitoring apparatus has a pressure sensor for measuring the pressure in the fluid system. During the blood treatment, the pressure in the fluid system is measured continuously, the leakage rate is determined from a possible change in the pressure, the leakage volume is calculated from the leakage rate, and the leakage volume is compared with a given limit value.

The problem addressed by the invention is that of avoiding a later interruption of a blood treatment if a defective dialyser of which the semi-permeable membrane has defects is used for the blood treatment.

The problem is solved according to the invention by the features of the independent claims. The dependent claims relate to advantageous embodiments of the invention.

The device according to the invention and the method according to the invention are based on the finding that a hydrophilic membrane wetted with liquid is impermeable to air provided that its pores do not exceed a specific size.

The amount of air which passes per unit of time through a defect in the semi-permeable membrane allows a conclusion to be drawn regarding the size of the defect. The relationship between the hole size and the volume flow is described approximately by the Hagen-Poiseuille law $dV/dt = \pi r^4 / 8\eta \Delta p / l$, where $\Delta p$ is the pressure difference, $\eta$ is the dynamic viscosity of the air, r is the pore size and l is the pore length of the membrane.

In the following, a semi-permeable membrane is understood as being any type of membrane that is used, for example, in plate dialysers and hollow fibre dialysers or hollow chamber filters. Hollow chamber filters have a bundle of hollow fibres arranged in a housing, the blood generally flowing through the hollow fibres and the dialysate flowing in the housing during the treatment. The regions inside and outside the fibres are, with the exception of the porous fibre walls, separated from one another in a fluid-tight manner, such that liquid is able to pass from the inside of the fibres to the outside region only through the fibre walls. The present invention likewise covers dialysers in which the blood flows outside the fibres and the dialysate flows inside the fibres.

The blood treatment device according to the invention has a fluid system which during operation includes the dialysate chamber, and a pump system for filling the fluid system including the dialysate chamber and for establishing a pressure difference between the blood chamber and the dialysate chamber, the pump system having at least one pump.

It is not important for the invention how the at least one pump for filling the fluid system or for establishing the pressure difference is controlled. For measuring the pressure in the fluid system including the dialysate chamber and for carrying out an integrity test for monitoring the integrity of the dialyser, the blood treatment device has a pressure measuring apparatus. A pressure measuring apparatus, which can have one or more pressure sensors, is generally present in a blood treatment device.

The fluid system including the dialysate chamber can be part of a larger fluid system, the hydraulic system. For the blood treatment device according to the invention and the method according to the invention, the fluid system including the dialysate chamber only has to comprise the semi-permeable membrane, since the integrity of said system is intended to be evaluated, and a pressure measuring apparatus for determining the pressure in the fluid system has to be provided. Furthermore, it has to be possible to fill said fluid system with liquid, to remove a portion of the liquid from that region by corresponding measures, and to generate a pressure gradient between the blood side of the semi-permeable membrane and the dialysate side of the semi-permeable membrane.

The blood treatment device additionally has a control and arithmetic unit which cooperates with the pump system and the pressure measuring apparatus and which provides a preparation mode in preparation for the blood treatment. A treatment mode is understood as being the operating state of the blood treatment device, in which the actual blood treatment takes place, that is to say the patient's blood is flowing through the blood chamber of the dialyser.

Monitoring of the integrity of the dialyser takes place not during the blood treatment, when the patient is connected to the extracorporeal blood circuit and blood from the patient is flowing through the blood chamber of the dialyser, but rather before the blood treatment in the preparation mode, which is provided by the control and arithmetic unit. If a defect is detected in the membrane of the dialyser, the dialyser can be changed before the patient is connected or before the blood flows through the blood chamber, such that the blood treatment does not later need to be interrupted. By checking the integrity of the dialyser before the blood treatment begins, safety for the patient is further increased because a blood treatment cannot be begun at all using a defective dialyser.

For carrying out the preparation mode, the control and arithmetic unit is so configured that the fluid system including the dialysate chamber is filled with a liquid, the integrity test for monitoring the integrity of the dialyser is carried out after the fluid system including the dialysate chamber has been filled with a liquid, and the blood chamber is filled with a liquid after the integrity test has been carried out. Consequently, the integrity test takes place at a time at which the blood chamber has not yet been filled with a liquid. The semi-permeable membrane of the dialyser has therefore not been wetted with liquid on the blood side before the integrity test is carried out. In other words, the blood chamber is for the most part dry. Only after the integrity test is the blood chamber filled with a liquid, for example with a preparation liquid (flushing liquid), in particular dialysate or another physiological liquid, in order to prepare the blood treatment device for carrying out the blood treatment. After the patient has been connected to the extracorporeal blood circuit, the flushing liquid can then be displaced by the patient's blood.

The invention is based on the finding that a membrane of a dialyser behaves differently for the integrity test when the blood chamber has not yet previously been filled with a liquid, that is to say the membrane has not been or is not wetted on the blood side. In other words, a blood chamber that has the membrane and has been filled once and then emptied again behaves differently in the integrity test than a membrane of a membrane that has not previously been filled. When wetted with a liquid on only one side or on both sides, the membrane is impermeable to air below a specific limit pressure. It has been shown that the test time of the integrity test can be shortened if the membrane is wetted on only one side.

For carrying out the integrity test, the control and arithmetic unit is so configured in the preparation mode that a pressure difference between the blood chamber and the dialysate chamber is established by means of the pump system in such a manner that the pressure in the blood chamber is greater than the pressure in the dialysate chamber. A pressure difference across the membrane of the dialyser is crucial for the integrity test. The pressure difference can be established by establishing a high pressure on the blood side or by establishing a low pressure on the dialysate side. A high pressure can be established by supplying liquid and a low pressure can be established by discharging liquid from the relevant chamber of the dialyser.

The pump system can have at least one pump for filling the dialysate chamber and at least one second pump for generating the pressure difference. The pressure difference can be generated, for example, by a pump by means of which liquid can be removed from the dialysate chamber, or the pressure difference can be generated by a pump by means of which air or liquid can be supplied to a fluid system that is fluidically connected to the blood chamber, such that the pressure in the blood chamber can be increased without liquid entering the blood chamber.

In a preferred embodiment, the control and arithmetic unit is so configured that, for establishing the pressure difference between the blood chamber and the dialysate chamber, liquid is removed by means of the pump system from the fluid system including the dialysate chamber or from the portion of the fluid system including the dialysate chamber, such that a low pressure is established in the dialysate chamber relative to the blood chamber. In order to establish a high pressure in the blood chamber, air or liquid can be supplied in the alternative embodiment to the extracorporeal blood circuit, which is closed to the outside. For example, there can be supplied to the blood hose system air via an air supply apparatus connected to the ventilation port or substituate by means of a substituate pump.

In preparation for the blood treatment, the fluid system including the dialysate chamber of the dialyser is first filled with a liquid, for example dialysate. During filling, air in the dialysate chamber can be discharged into the open hose system of the extracorporeal blood circuit via the membrane of the dialyser. As soon as all the pores of the membrane on the dialysate side are wetted with liquid, the pressure in the dialysate chamber increases sharply if the fluid system is a closed volume, since a membrane, wetted with liquid, of which the pores do not exceed a specific size is impermeable to air.

After the fluid system including the dialysate chamber or the portion of the fluid system has been filled with a liquid, the fluid system or a portion of the fluid system can be flushed with the liquid. However, flushing of the fluid system is not absolutely essential for checking the integrity of the dialyser. However, flushing makes it possible to remove air from the dialysate chamber, which can have an influence on the later determination of compliance and the integrity test. In this case, the air is flushed out, for example, in the direction of the drain for the dialysate from the dialysate chamber.

It is not necessary to use the entire fluid system, which includes the dialysate chamber of the dialyser, for checking the integrity of the dialyser. It is sufficient to fill the portion of the hydraulic system that includes the dialysate chamber and to carry out the test in that portion. For this purpose, that portion can be separated from the remainder of the fluid system. Separation of the relevant portions of the fluid system can be effected by the actuation of valves, provided in the fluid system, by the control and arithmetic unit.

In the preferred embodiment, after the membrane has been wetted with liquid on the dialysate chamber side during the filling operation, liquid is removed from the fluid system including the dialysate chamber or from the portion of the fluid system, such that a low pressure is established in the fluid system or the portion of the fluid system relative to the blood chamber, since an intact membrane is impermeable to air. It should be noted that this is a pressure hold test for the membrane such that, when a low pressure is described, it relates to the ratio of the pressures between the dialysate chamber and the blood chamber. The absolute pressures with regard to atmospheric pressure are unimportant. For determining the pressure difference between the dialysate chamber and the blood chamber, a pressure measuring apparatus can be provided for the blood chamber. However, provided that the pressure on the blood side does not change, for example because it is aerated or because there is no or only a slight movement of air from or into the blood side, it is also possible to use solely the pressure changes on the dialysate side. Therefore, all the present descriptions of pressure changes and the measurement or determination thereof also include the case where, instead of the pressure on the dialysate side alone, a pressure difference between the dialysate side and the blood side is used.

The control and arithmetic unit is so configured that the increase in the pressure, measured by the pressure measuring apparatus, in a given time interval is determined, and a leakage rate of the fluid system is determined from the increase in the pressure in a given time interval and the compliance of the fluid system including the dialysate chamber. The compliance of the fluid system including the dialysate chamber can be a given (known) value, which can be stored in a memory of the control and arithmetic unit, or it can be a value which is determined in the preparation mode.

A conclusion is then drawn regarding a lack of integrity of the dialyser on the basis of the determined leakage rate, in which the compliance of the fluid system is taken into consideration. The leakage rate should be below a limit value if the dialyser is intact. It is in this case assumed that the membrane of a dialyser which is tight, that is to say of which the pores do not exceed a specific size, is impermeable to air, and therefore a low pressure can be established when liquid is removed.

It has been shown in practice that the compliance of the fluid system has an influence on pressure changes which cannot be ignored. Therefore, the invention is based on the principle of taking into consideration the compliance of the fluid system or of the portion of the fluid system including the dialysate chamber when determining the leakage rate. The properties of the dialyser or of different hose sets or cassettes, but also method properties such as the filling process, can therefore also be taken into consideration during the monitoring. By taking the compliance into consideration, accurate leakage measurement is therefore possible. Since only the hydraulic side of the dialyser is filled with liquid, but the blood side of the dialyser is not filled with liquid, incorrect leakage measurement owing to the passage of liquid through the membrane of the dialyser can be prevented. In addition, the measuring time can be shortened. Depending on the configuration of the integrity test, the compliance of the fluid system can be determined at the same time as liquid is removed.

The compliance can be determined on the basis of a pressure change resulting from a volume change. For this purpose, a given volume of liquid is removed from or supplied to the fluid system, it being possible for the compliance to be calculated on the basis of the pressure change in the fluid system. The pressure changes increase as the compliance falls, or decrease as the compliance increases, that is to say the greater the flexibility or the lower the stiffness of the system, the smaller the pressure changes. For example, the pressure changes are relatively small when the walls of the hose lines or of the cassette deform relatively greatly. When liquid is discharged from the fluid system in order to determine the compliance, the pressure in the system does not need to be raised, and therefore a specific limit pressure cannot be exceeded.

One embodiment of the blood treatment device according to the invention provides that the control and arithmetic unit is so configured that, for monitoring the integrity of the dialyser, in the preparation mode the compliance is calculated from the volume of liquid that is removed in the given time interval from the fluid system including the dialysate chamber or from the portion of the fluid system, and the fall in the pressure measured by the pressure measuring apparatus.

Since such systems can require a long time until the pressure values stabilise, it can be provided that the change in the pressure in a given time interval is determined and/or that the compliance is determined using a pressure value at which a rate of pressure change is below a limit value.

For the integrity test, the determined leakage rate can be compared with a given limit value for the leakage rate and it can be concluded that there is a leak, and a control signal signalling the lack of integrity of the dialyser can be generated if the leakage rate does not fall below the given limit value in a given time interval. If the leakage rate falls below the given limit value before the given time interval has passed, the test can be terminated and it can be concluded that the dialyser is in order, and a control signal signalling the sufficient integrity of the dialyser can be generated.

In other words, the leakage rate is determined continuously or at at least one specific time or at a plurality of predetermined times. If one or more of the determined leakage rates is below a given limit value, the system is considered to be tight and a treatment can subsequently be carried out. A certain leakage rate can be accepted because, even in the case of an intact membrane, pressure can build up in a different way, for example as a result of ports that are not tight or a system that changes over time or with temperature variations.

In dependence on the control signal, the user can be notified, for example an alarm can be triggered, and/or a message can be displayed on a screen, and/or a suitable intervention in the machine control system can take place.

The removal of liquid from the fluid system in order to establish the low pressure preferably takes place by means of the ultrafiltrate pump of an ultrafiltration apparatus, in order to be able to remove liquid from the fluid system. An ultrafiltration apparatus is generally part of the pump system of the known blood treatment devices. However, the liquid can also be pumped away by a different pump in the fluid system. In this respect, it is known to a person skilled in the art that the ultrafiltration unit can be integrated into a balancing unit. This can be achieved if the ultrafiltration pump is at the same time part of the balancing pump system and ultrafiltration takes place merely by different pump speeds for the supply and discharge of liquid.

The invention is described in detail below with reference to the figures, in which.

Figure 1:
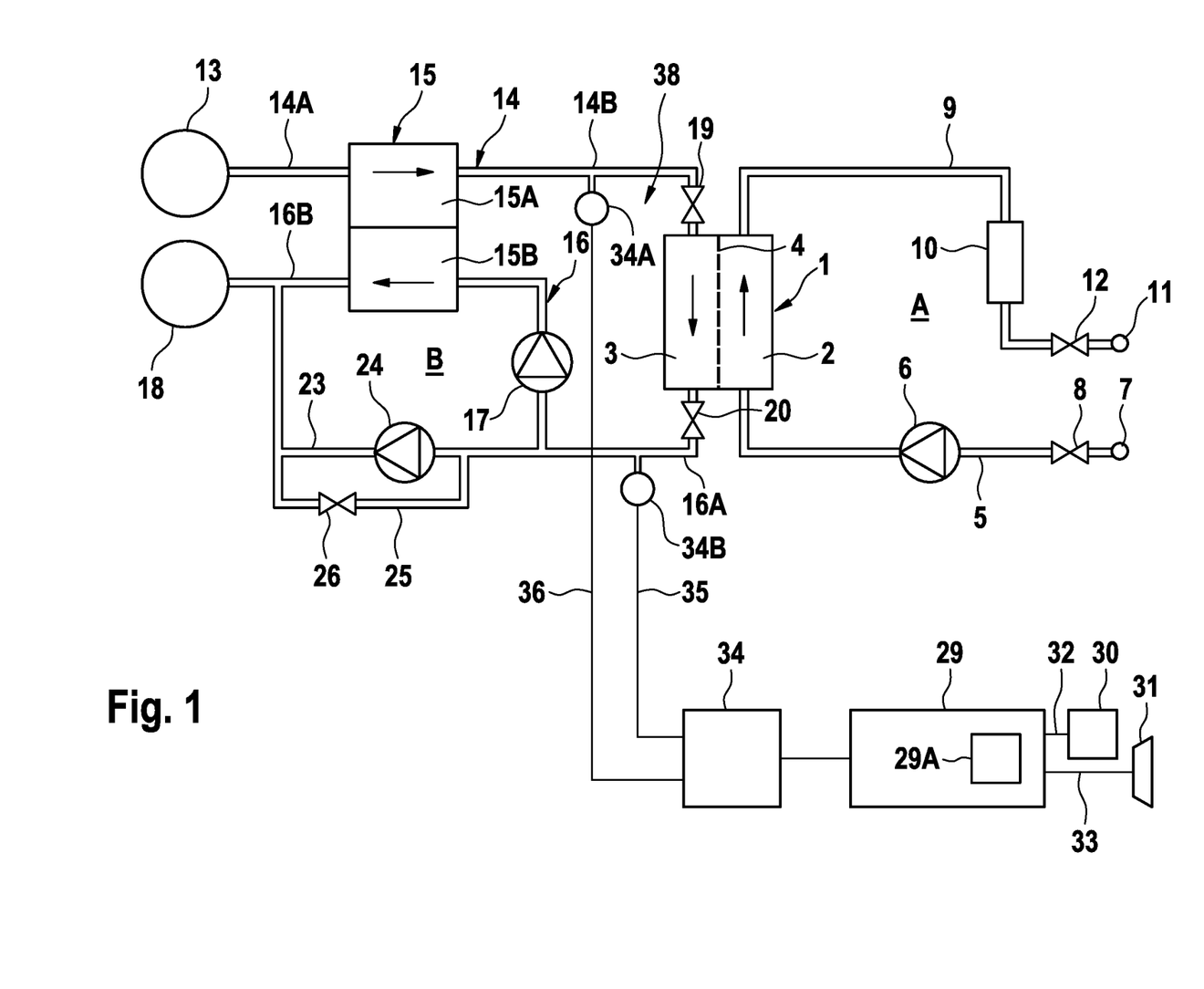
FIG. 1 is a simplified schematic view of an embodiment of a blood treatment device according to the invention.

FIG. 1 is a highly simplified schematic view of the components of a blood treatment device according to the invention. The blood treatment device comprises an extracorporeal blood circuit A and a fluid system B. The extracorporeal blood circuit A includes the blood chamber 2, and the fluid system B includes the dialysate chamber 3 of a dialyser 1. The blood chamber 2 and the dialysate chamber 3 of the dialyser 1 are separated by a semi-permeable membrane 4. A blood supply line 5, in which a blood pump 6 is provided, leads from an arterial patient port 7 to the inlet of the blood chamber 2. Upstream of the blood pump 6, an arterial valve 8 can be situated in the blood supply line 5. From the outlet of the blood chamber 2, a blood discharge line 9, in which a liquid chamber (drip chamber) 10 can be connected, leads to a venous patient port 11. Downstream of the liquid chamber 10, a venous valve 12 is situated in the blood discharge line 9.

The extracorporeal blood circuit A and the fluid system B, or portions of the extracorporeal blood circuit or of the fluid system B, can be in the form of disposables intended for single use. In the following, the blood treatment device is described in the ready state, in which the disposable or disposables have been inserted into or fastened to the blood treatment device.

The fluid system B can further have a dialysate source 13 for providing fresh dialysate, which is connected via a first portion 14A of a dialysate supply line 14 to the inlet of a chamber 15A of a balancing unit 15. The second portion 14B of the dialysate supply line connects the outlet of one chamber 15A of the balancing unit 15 to the inlet of the dialysate chamber 3. The dialysate can be used as flushing or preparation liquid.

The outlet of the dialysate chamber 3 is connected via a first portion 16A of a dialysate discharge line 16 to the inlet of the other chamber 15B of the balancing unit 15. A dialysate pump 17 is situated in the first portion 16A of the dialysate discharge line 16. The outlet of the other chamber 15B of the balancing unit 15 is connected via the second portion 16B of the dialysate discharge line 16 to a drain 18. The balancing unit 15 can have further chambers.

A valve 19 is situated in the dialysate supply line 14 upstream of the dialysate chamber 3, and a valve 20 is situated in the dialysate discharge line 16 downstream of the dialysate chamber 3. The valves 19, 20 can be electromagnetically operable valves. From the first portion 16A of the dialysate discharge line 16, an ultrafiltrate line 23, in which an ultrafiltrate pump 24 is provided, leads to the second portion 16B of the dialysate discharge line 16. From a portion of the ultrafiltrate line 23 upstream of the ultrafiltrate pump 24, a bypass line 25, in which a bypass valve 26 is provided, can lead to a portion of the ultrafiltrate line 23 downstream of the ultrafiltrate pump 24. The blood pump 6, the dialysate pump 17 and the ultrafiltrate pump 24 can be occluding pumps. When the pumps are occluding pumps, valves for creating a closed volume can be omitted.

In the present embodiment, the blood supply and discharge lines 5, 9 of the extracorporeal blood circuit A are part of an exchangeable blood hose set, and the dialysate supply and discharge lines 14, 16 of the dialysate system B are fixed parts of the hydraulic system of the blood treatment device. The blood hose set and the dialyser 1 are intended for single use and are inserted in receivers (not shown). Instead of a hose set, it is also possible to provide an exchangeable cassette in which channels for the liquid, in particular the supply and discharge of blood, are formed. The receiver for the dialyser can be a holder.

The blood treatment device has a central control and arithmetic unit 29 for controlling all the components of the device. The central control and arithmetic unit 29 can have, for example, a general processor, a digital signal processor (DSP) for continuously processing digital signals, a microprocessor, an application-specific integrated circuit (ASIC), an integrated circuit consisting of logic elements (FPGA), or other integrated circuits (IC) or hardware components, in order to perform the individual method steps for controlling the blood treatment device. A data processing program (software) can run on the hardware components for performing the method steps. A plurality or a combination of the various components is also possible.

The control and arithmetic unit 29 is connected via control or data lines (not shown) to the pumps 6, 17, 24, the valves 8, 12, 19, 20 and the bypass valve 26, such that the flow rates of the pumps can be adjusted and the valves and the bypass valve can be actuated. The pumps 6, 17, 24, valves 8, 12, 19, 20 and the bypass valve 26 are part of a pump system 38 of the blood treatment device.

The control and arithmetic unit 29 has a memory 29A in which measured values and parameters can be stored. Furthermore, a display unit 30 and an alarm unit 31 are provided, which are connected via data lines 32, 33 to the control and arithmetic unit 29. The display unit 30 can have display elements, for example signal lamps, or a display for displaying various symbols, which indicate that the dialyser is in order or that the dialyser lacks integrity. The alarm unit 31 can have a signal generator for an acoustic and/or optical and/or tactile alarm.

The pressure in the fluid system B is measured by means of a pressure measuring apparatus 34. The pressure measuring apparatus 34 can have a first pressure sensor 34A which measures the pressure in the second portion 14B of the dialysate supply line 14, and/or have a second pressure sensor 34B which measures the pressure in the first portion 16A of the dialysate discharge line 16. The control and arithmetic unit 29 receives the signals from the pressure measuring apparatus 32 via data lines 35, 36. The measured pressure values are stored in the memory 29A of the control and arithmetic unit 29 for the calculation of various values.

The known blood treatment devices provide a treatment mode and a preparation mode preceding the treatment, in preparation for the treatment. During the actual blood treatment, the extracorporeal blood circuit A, which comprises the blood supply line 5, the blood chamber 2 of the dialyser 1 and the blood return line 9, is filled with blood, which is conveyed by the blood pump 6. In the preparation mode preceding the blood treatment, the blood chamber is not filled with blood.

The control and arithmetic unit 29 is so configured that the preparation mode or the treatment mode can be specified. Monitoring of the integrity of the membrane 3 of the dialyser 1 takes place in the preparation mode during a filling and flushing process, which is carried out in any case in preparation for the blood treatment. For the integrity test, the control and arithmetic unit 29 controls the individual components of the blood treatment device as follows, in order to carry out the following method steps.

The control and arithmetic unit 29 opens the valve 19 of the pump system 38 in the dialysate supply line 14 upstream of the dialysate chamber 3 and can close the valve 20 in the dialysate discharge line 16 downstream of the dialysate chamber 3. Dialysate is then conveyed from the dialysate source via the balancing unit 15 to the dialysate chamber 3. The filling pressure of the dialysate chamber 3 is measured by the pressure sensor 34A for measuring the pressure in the dialysate supply line 14 and monitored by the control and arithmetic unit 29. The air in the dialysate chamber 3 is thus able to escape via the membrane 4 of the dialyser into the blood chamber 2 and from the blood chamber via the open hose system of the extracorporeal blood circuit A. As soon as all the pores of the membrane 4 are wetted, the pressure in the dialysate supply line 14 increases sharply. When the filling pressure exceeds a given limit value, which is stored in the memory 29A, the control and arithmetic unit 29 opens the valve 20 in the dialysate discharge line 16, such that the dialysate chamber 3 is vigorously flushed, the dialysate flowing into the drain 18. The pressure in the dialysate supply line 14 then falls below the limit value again.

Alternatively, the valve 20 can also be opened, and further regions, depending on the position of the valves that are present, are filled.

The fluid system B including the dialysate chamber 3 can now be further flushed with dialysate with the valve 20 open, and therefore the hydraulic system is further ventilated. At the end of the flushing operation, the valve 19 in the dialysate supply line 14 is closed again. The membrane 4 of the dialyser 1 is now wetted with dialysate on the hydraulic side, and therefore the membrane is air-tight. On the blood side, however, the membrane has not been wetted with liquid, since the blood chamber has not yet been filled with blood. In the case of a hollow chamber filter, the lumen of the fibres of the membrane are still empty. As a result, the integrity test can be carried out in a relatively short time.

After the flushing operation, liquid, which in the present embodiment is dialysate as flushing liquid, is removed from at least a portion of the fluid system B including the dialysate chamber 3. In order to remove liquid, the control and arithmetic unit 29 operates the ultrafiltrate pump 24, the valve 19 in the dialysate supply line 14 being closed. The valve 26 in the bypass line 25 is likewise closed.

It should be noted at this point that, according to the invention, the fluid system B, during operation, only has to include the dialysate chamber and a pressure measuring apparatus. Further components shown may or may not be present, or may or may not belong to the fluid system B. Ultimately, any region of the hydraulic system can belong to the fluid system B according to the invention provided that there is a region which can be filled with liquid and from which liquid can be removed and in which the pressure can be measured and which also includes the dialysate chamber. In addition, this region should also be suitable for being shut off in a pressure-tight manner such that the pressure changes required for the pressure test described herein can be determined.

The use of an ultrafiltrate pump for removing the liquid has the advantage that a specific volume of liquid can be removed very accurately by means of this pump. This is a requirement for the correct use of an ultrafiltrate pump during the blood treatment. There are therefore used as ultrafiltrate pumps in blood treatment devices only pump types which, as a result of their construction, are able to remove from the system volumes which can be defined exactly. The ultrafiltrate pump can be a membrane pump. Alternatively, however, different pumps can be used. For example, a dialysate pump having a flow meter, for example having a Coriolis flow meter, can be used for pumping away the liquid.

In the present embodiment, in the dialysate discharge line 16 the pressure $p_{t1}$ is measured before one or each pump stroke and the pressure $p_{t2}$ is measured after one or each pump stroke. For at least one or each pump stroke, the control and arithmetic unit 29 calculates the compliance C of the portion of the fluid system B including the dialyser 1 from the known volume dV of a pump stroke and from the measured pressure $p_{t1}$, $p_{t2}$ before and after the relevant pump stroke. The compliance values, which are stored in the memory 29A, are calculated according to the following equation:

$$C=dV/(p_{t2}-p_{t1})$$

For the integrity test, it is necessary to generate a pressure difference across the membrane. In one embodiment, when the liquid is removed by means of the ultrafiltrate pump 24, a low pressure is established in the fluid system B that includes the dialysate chamber 3, since the wetted membrane 4 of the dialyser 1 is largely air-tight even if the membrane has defects, because the volume of air which could pass into the fluid system via the defects is low in relation to the volume of liquid that is removed.

The pressure is measured by means of the pressure sensor 34B in the dialysate discharge line 16. The ultrafiltrate pump 24 is operated until a given test pressure has been established. For this purpose, the current measured pressure can continuously be compared with the given test pressure. Since the compliance is determined at least for the last pump stroke, the compliance at the test pressure is also known. In a preferred embodiment, the compliance value determined at the test pressure is used as the basis for the further analysis. It is not necessary in this case to determine the compliance values for each pump stroke. However, it is also possible to use an average value for the compliance or a maximum or minimum compliance value as the basis for the further analysis.

If the test pressure has not been established even after a given maximum delivery volume of the ultrafiltrate pump 24, it is already concluded in advance that the membrane 4 of the dialyser 1 is not tight. It can also be concluded that there is a leak if the test pressure has not been established after a given time interval in which the ultrafiltrate pump has been running. If that is the case, the control and arithmetic unit 29 generates a control signal which signals the lack of integrity of the dialyser 1 and which is received by the display unit 30 and/or the alarm unit 31. The fact that the dialyser lacks integrity can then be displayed on the display unit 30 and/or an alarm can be given by the alarm unit 31. The defective dialyser must then be replaced by a new dialyser.

The actual integrity test then takes place, by means of which the integrity of the dialyser can reliably be checked in a relatively short test time, it being possible for even slight leaks to be detected.

The low pressure increases during operation of the ultrafiltrate pump 24, in other words the pressure difference relative to the blood chamber becomes increasingly greater. If the test low pressure for the integrity test is reached, the integrity test can begin. For this purpose, the change in the pressure over time in the closed fluid system B is measured and the rate of pressure increase $\Delta p/t_A-t_B = p_{tA}-p_{tB}/t_A-t_B$ is determined, where $p_{tA}$ is the pressure measured at time $t_A$, and $p_{tB}$ is the pressure measured at the later time $t_B$, and $t_A-t_B$ is the time interval between the start of the measurement at $t_A$ and the later time $t_B$.

From the rate of pressure increase and the compliance C determined, for example, for the last pump stroke, that is to say the compliance at the test pressure, the control and arithmetic unit 29 calculates the leakage rate LR according to the following equation:

$$LR=C\Delta p/t_A-t_B$$

Since this determination of LR can take place continuously or at one or more predetermined times, an averaged leakage rate for the time interval $t_A$ to $t_B$ is calculated.

The calculated leakage rate LR is compared with a given limit value for the leakage rate LR, which is assumed for an intact dialyser. If the calculated leakage rate LR is smaller than the given limit value, it is concluded that the dialyser is intact. The control and arithmetic unit 29 can then send a control signal signalling the integrity of the dialyser to the display unit 30, which is displayed on the display unit. The control and arithmetic unit 29 can also generate a control signal which carries out an intervention in the machine control system. For example, specification of the treatment mode can be prevented following detection of a membrane that is not tight, or the treatment mode can be enabled only if sufficient integrity of the dialyser is detected.

For the integrity test, a maximum test time is specified, in which liquid is removed from the fluid system in order to establish the low pressure. If the calculated leakage rate LR is not smaller than the given limit value during the maximum test time, it is concluded that the membrane 4 is not tight. In this case, the control and arithmetic unit 29 generates a control signal signalling the lack of integrity of the dialyser 1, which is received by the display unit 30 and/or the alarm unit 31, such that it is then indicated on the display unit that the membrane of the dialyser is not tight, and an alarm is given by the alarm unit. The control and arithmetic unit 29 can also generate a control signal which carries out an intervention in the machine control system such that the blood treatment mode is not enabled, such that it is not possible to carry out a treatment using a defective dialyser.

In the present embodiment, the ultrafiltrate pump 24 is operated cyclically. It is also possible to calculate the compliance C and the leakage rate LR, taking the compliance C into consideration, for each cycle (pump stroke) or to determine the compliance and the leakage rate for any given time interval, which can include a plurality of pump strokes.

In the case of a leakage rate which is greater than zero, the test pressure in the fluid system can readily fall. However, the measurement result can be distorted thereby only slightly. In order to avoid this measurement error, the control and arithmetic unit 29 can be so configured that the ultrafiltrate pump 24 is so controlled that the given test pressure established in the portion of the fluid system including the dialysate chamber 3 is kept constant. For this purpose, a delivery rate for the ultrafiltrate pump 24 is set. Since the test pressure falls according to the leakage rate, the delivery rate of the ultrafiltration pump 24 must directly correspond to the leakage rate in order to keep the test pressure constant. In this embodiment, the control device has a pressure-based feedback control for keeping the test pressure constant. In this embodiment, the blood treatment device, or the method, thus has to be configured to determine the leakage rate without explicitly determining the compliance and to thus carry out the integrity test according to the above description. The compliance is taken into consideration inherently in the feedback control, in that the dynamics of the pressure response of the system already depends on the compliance.

In a further embodiment, the pressure difference is generated by building up pressure in the blood chamber. For this purpose, the pressure in the blood chamber can be increased by supplying air or liquid to the extracorporeal blood circuit (A), without filling the blood chamber with liquid. Otherwise, the above observations relating to the establishment of the pressure difference by decreasing the pressure in the dialysate chamber apply analogously.

Figure 2:
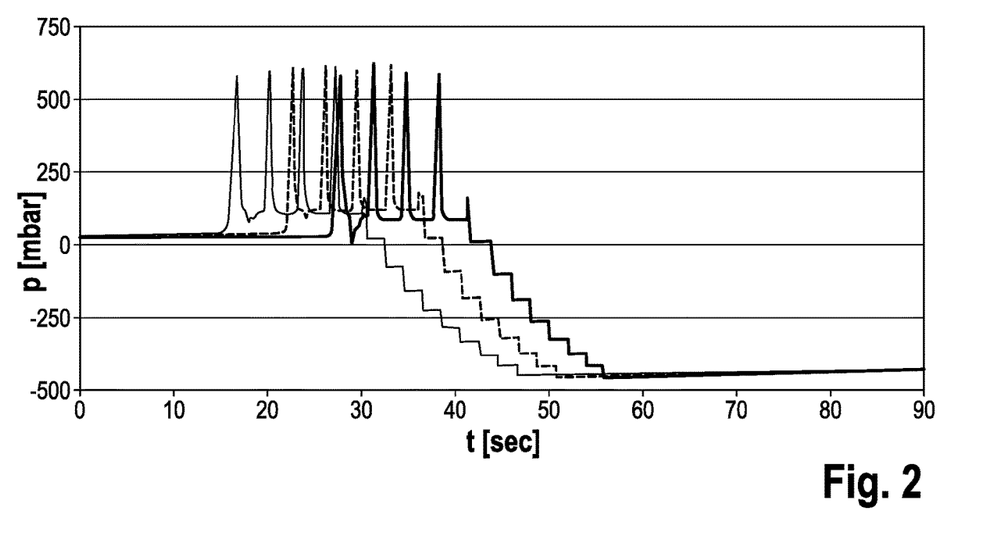
FIG. 2 shows the pressure in the fluid system as a function of time for different dialysers.

FIG. 2 shows the change over time in the low pressure p measured by means of the pressure sensor 34B in the blood discharge line 16, while the ultrafiltrate pump 24 removes liquid from the fluid system. The low pressure for three different dialyser types is shown in FIG. 2. It is shown that the low pressure increases while liquid is being removed from the fluid system. With each pump stroke, the low pressure increases stepwise by a specific amount until the test pressure is reached. Furthermore, it can be seen that there is a slight rise after the last ultrafiltration pump stroke. The leakage rate LR is then determined from this rise.

Figure 3:
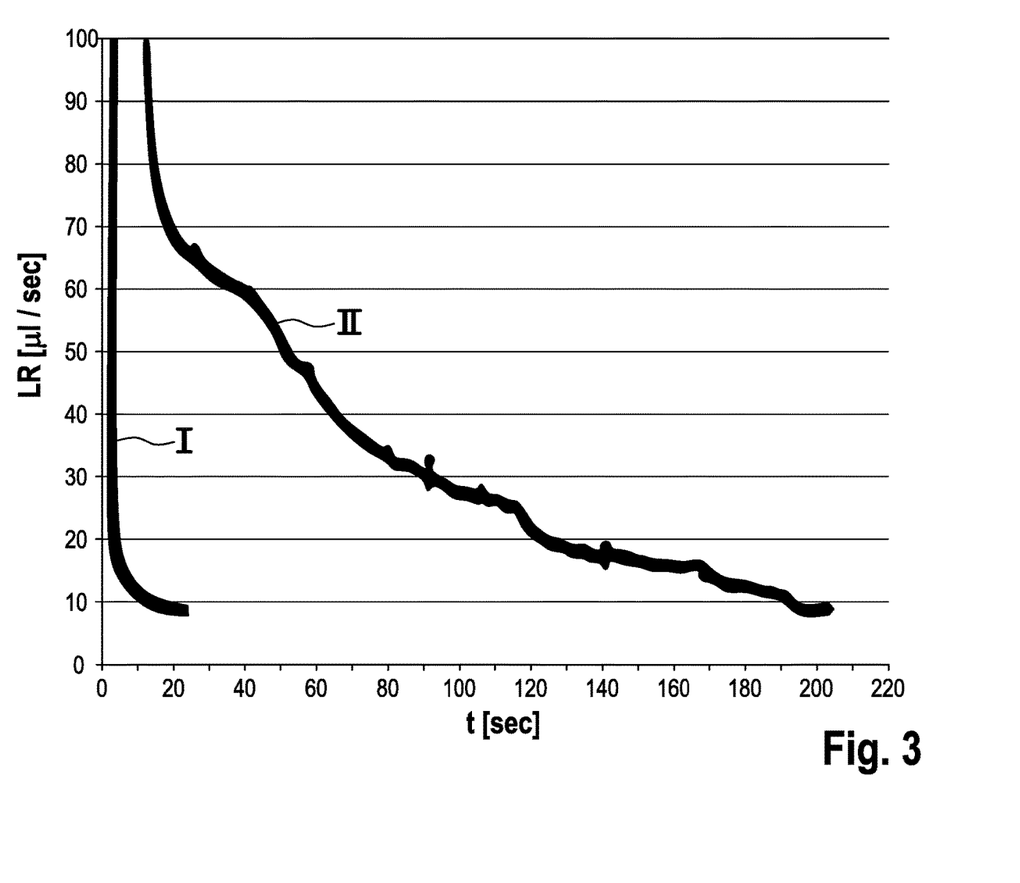
FIG. 3 shows the pressure in the fluid system as a function of time for the integrity test according to the invention in which the dialyser is filled with a liquid only on the dialysate side and for an integrity test in which the blood side of the dialyser was also filled with a liquid.

FIG. 3 shows the change over time in the leakage rate LR in the case of a measurement using a dialyser of which the dialysate chamber is filled with liquid, the blood chamber having been filled with liquid once (graph II), in comparison with a dialyser of which the dialysate chamber is filled with liquid, the blood chamber not having been filled with liquid (graph I). It is shown that a minimum leakage rate LR is reached after only about 20 seconds in the case of a dialyser of which the blood chamber was not filled with liquid, while the minimum leakage rate LR is reached only after about 200 seconds in the case of a dialyser of which the blood chamber was filled with liquid. Consequently, the measuring time for checking the integrity of the dialyser membrane can be shortened significantly using the method according to the invention as compared with a conventional method.

After the integrity test, the extracorporeal blood circuit A is filled with a preparation liquid. Only after filling with the preparation liquid, for example dialysate, is the membrane of the dialyser wetted with liquid also on the blood side. For filling the blood chamber with a pre-liquid in the preparation mode, liquid from the hydraulic system B or liquid from a container can be supplied to the extracorporeal blood circuit A. For flushing the extracorporeal circuit A, the flushing liquid can, via a connection, be supplied to the fluid system A or guided into a separate container.

The invention claimed is:

1. An extracorporeal blood treatment device for carrying out an extracorporeal blood treatment, in which blood flows in an extracorporeal blood circuit through a blood chamber of a dialyser that is separated by a semi-permeable membrane into the blood chamber and a dialysate chamber, the dialysate chamber comprising an inlet and an outlet, the extracorporeal blood treatment device comprising:

the dialyser, a fluid system comprising at least the dialysate chamber of the dialyser, a dialysate supply line connected to the inlet, and a dialysate discharge line connected to the outlet, a pump system for filling the fluid system, including the dialysate chamber, with a liquid, and for establishing a pressure difference between the blood chamber and the dialysate chamber, the pump system comprising a blood pump and at least one pump for filling the fluid system, a pressure measuring apparatus, comprising one or more pressure sensors, for measuring pressure in the fluid system, including in the dialysate chamber, for carrying out an integrity test for monitoring integrity of the dialyser, and a control and arithmetic unit that cooperates with the pump system and the pressure measuring apparatus and that provides a preparation mode in preparation for the extracorporeal blood treatment, wherein for carrying out the preparation mode, the control and arithmetic unit is configured such that:

the fluid system, including the dialysate chamber, is filled with the liquid, the integrity test for monitoring the integrity of the dialyser is carried out after the fluid system, including the dialysate chamber, has been filled with the liquid, the blood chamber is filled with a liquid after the integrity test has been carried out, the integrity test is carried out by the control and arithmetic unit in the preparation mode such that a pressure difference is established between the blood chamber and the dialysate chamber in such a manner that the pressure in the blood chamber is greater than the pressure in the dialysate chamber, an increase in pressure p, measured by the pressure measuring apparatus, in a given time interval, is determined, by the control and arithmetic unit, a leakage rate LR is determined, by the control and arithmetic unit, from the measured increase in the pressure p in the given time interval, and from a compliance C of the fluid system including the dialysate chamber, C being determined by the control and arithmetic unit, and a lack of integrity of the dialyser is concluded, by the control and arithmetic unit, on the basis of the leakage rate LR, and wherein the control and arithmetic unit generates an intervention control signal upon concluding the lack of integrity of the dialyzer, and cooperates with the pump system, based on the intervention control signal, to carry out an intervention whereby operation of the extracorporeal blood treatment device in the treatment mode is prevented.

2. The extracorporeal blood treatment device according to claim 1, wherein the control and arithmetic unit is so configured that, for establishing the pressure difference between the blood chamber and the dialysate chamber, either liquid is removed, by means of the pump system, from the fluid system including the dialysate chamber, or the pressure in the blood chamber is increased by means of the pump system.

3. The extracorporeal blood treatment device according to claim 2, wherein the pump system has an ultrafiltrate pump, and the control and arithmetic unit is so configured that the ultrafiltrate pump is operated to remove liquid from the fluid system including the dialysate chamber, such that a fall in pressure occurs in the fluid system including the dialysate chamber.

4. The extracorporeal blood treatment device according to claim 1, wherein the control and arithmetic unit is so configured that the leakage rate LR is calculated according to the following equation:

$$LR = C\, dp/dt$$

where C is the compliance of the fluid system including the dialysate chamber, and dp/dt is a rate of pressure increase.

5. The extracorporeal blood treatment device according to claim 1, wherein the control and arithmetic unit is so configured that, for monitoring the integrity of the dialyser in the preparation mode, the compliance C is calculated from a volume of the liquid that is removed from the fluid system including the dialysate chamber, and a fall in the pressure measured by means of the pressure measuring apparatus.

6. The extracorporeal blood treatment device according to claim 5, wherein the control and arithmetic unit is so configured that the compliance C is calculated according to the following equation:

$$C = dV/dp$$

where dV is the volume of the liquid removed from the fluid system including the dialysate chamber, and dp is the fall in pressure during the time interval from before removal of the liquid until after the removal of the liquid.

7. The extracorporeal blood treatment device according to claim 1, wherein the control and arithmetic unit is so configured that the leakage rate LR is compared with a given limit value for the leakage rate, and the lack of integrity is concluded if the leakage rate does not fall below the given limit value in a given time interval.

8. The extracorporeal blood treatment device according to claim 1, wherein the control and arithmetic unit is so configured that, in the preparation mode, after the fluid system including the dialysate chamber has been filled with a liquid, the fluid system is flushed.

9. The extracorporeal blood treatment device according to claim 1, wherein the fluid system further comprises a balancing chamber.

10. The extracorporeal blood treatment device according to claim 1, wherein the extracorporeal blood circuit comprises a blood supply line that leads to the blood chamber of the dialyser and a blood discharge line that leads away from the blood chamber.

11. The extracorporeal blood treatment device according to claim 10, wherein the blood pump is provided on the blood supply line, and the at least one pump for filling the fluid system comprises a dialysate pump provided on the dialysate discharge line.

12. The extracorporeal blood treatment device according to claim 10, wherein the pump system further comprises an arterial valve provided on the blood supply line, a venous valve provided on the blood discharge line, a first dialysate valve provided on the dialysate supply line, and a second dialysate valve provided on the dialysate discharge line.

* * * * *